United States Patent [19]

Martinsen et al.

[11] Patent Number: 5,738,107
[45] Date of Patent: Apr. 14, 1998

[54] MEASUREMENT OF MOISTURE CONTENT IN SKIN

[76] Inventors: Ørjan G. Martinsen, Fagerstrandvn. 30, N-1320 Stabekk; Sverre Grimnes, Uranienborgvn. 10, N-0258 Oslo, both of Norway

[21] Appl. No.: 817,350

[22] PCT Filed: Oct. 9, 1995

[86] PCT No.: PCT/NO95/00184

§ 371 Date: Apr. 10, 1997

§ 102(e) Date: Apr. 10, 1997

[87] PCT Pub. No.: WO96/10951

PCT Pub. Date: Apr. 18, 1996

[30] Foreign Application Priority Data

Oct. 11, 1994 [NO] Norway ........................ 943840

[51] Int. Cl.⁶ .................................................. A61B 5/05
[52] U.S. Cl. ............................................... 128/734
[58] Field of Search ............................. 128/632, 630, 128/639, 642, 734, 735, 741

[56] References Cited

U.S. PATENT DOCUMENTS

| | | | |
|---|---|---|---|
| 4,013,065 | 3/1977 | Copeland et al. | 128/2 R |
| 4,174,498 | 11/1979 | Preikschat | 324/57 R |
| 4,860,753 | 8/1989 | Amerena | 128/632 |
| 4,966,158 | 10/1990 | Honma et al. | 128/734 |
| 5,353,802 | 10/1994 | Ollmar | 128/734 |

FOREIGN PATENT DOCUMENTS

| | | |
|---|---|---|
| 1192749 | 5/1970 | United Kingdom . |
| WO 92/06634 | 4/1992 | WIPO . |

OTHER PUBLICATIONS

"An Instrument for the Evaluation of Skin Hydration by Electrical Admittance Measurements", Martinsen et al., Innov. Tech. Biol. Med., vol. 14, No. 5, pp. 588–596, 1993.
"Impedance measurement of individual skin surface electrodes", Grimnes, S., Medical and Biological Engineering & Computing, vol. 21, pp. 750–755, Nov. 1983.

Primary Examiner—Francis Jaworski
Attorney, Agent, or Firm—Morgan, Lewis & Bockius LLP

[57] ABSTRACT

In order to measure the moisture content in skin, especially in the keratinous layer (stratum corneum), at least two electrodes are employed, at least one of which electrodes is placed on the skin where moisture has to be measured, the electrodes are supplied with a periodic voltage with a frequency of less than 50 kHz, and the susceptance in the keratinous layer is measured beneath the electrode or electrodes. In an apparatus for measuring the moisture content in skin three electrodes are employed, a periodic voltage being applied to two of these. The susceptance is measured below one of the electrodes, uninfluenced by the other electrodes, the measurement thus being truly monopolar.

14 Claims, 3 Drawing Sheets

MEASUREMENT OF MOISTURE CONTENT IN SKIN

BACKGROUND OF THE INVENTION

The invention concerns a method for measuring the moisture content in skin, especially in the keratinous layer (stratum corneum), as stated in the introduction of claim 1. The invention also concerns an apparatus for monopolar measurement of the moisture content in skin, especially in the keratinous layer (stratum corneum), as stated in the introduction of claim 7.

An evaluation of the degree of hydration of the stratum corneum by measuring the skin's electrical properties is a challenge, involving the difficult problem of relating electrical parameters to physiological conditions. It is of vital importance to obtain improved methods and apparatus for measuring the moisture or hydration in the stratum corneum, since the moisture content in the skin is closely dependent on the function of the skin, and measuring the state of hydration of the stratum corneum can enable an early diagnosis to be obtained of non-visible conditions in the skin. Electrical measurements of the skin's moisture content are also valuable for evaluating a number of different factors, for example for assessing the effect of medicaments, cosmetics, moisturizers and other skin care preparations for the moisture content in the skin.

Apparatus for measuring moisture in a substance by using the electrical parameters of the substance, are e.g. known from U.S. Pat. No. 4,174,498 which teaches an apparatus for find the moisture content of particular materials. The determination of moisture takes place by combining conductance and susceptance signals, while assuming that the substance has an electrically homogenous volume.

Modern moisturizers and similar skin care preparations are increasingly based on liposomes, where an aqueous volume is completely surrounded by one or more double membranes consisting of lipide molecules. These are formed spontaneously when the lipids (usually phosphoric lipids) are dispersed in aqueous media and can range in diameter from tens of nm to tens of micrometres. New skin care products therefore are increasingly utilizing liposomes in order to facilitate the transport of active substances into the skin. Intact liposomes only penetrate the stratum corneum, and since they are hygroscopic and capable of containing a volume of water equal to many times their phosphoric lipide weight, they will cause an increase in the moisture content of the skin.

In order to measure the effect of such skin care preparations, instruments have been employed of the type "Corneometer" and "Skicon", of which the latter is described in Tagami H. & al., "Evaluation of the skin surface hydration in vivo by electrical measurement", J.Invest. Dermatol. 75, 1980, pp. 500–507. These work on frequencies from approximately 100 kHz to several MHz where the impedance of the stratum corneum is low, thus making it difficult to obtain an isolated measurement of, for example, the admittance in the stratum corneum. Furthermore there is the possibility that two adjacent surface electrodes on the skin will be short-circuited due to skin cream, perspiration, etc.

International Patent Application WO92/06634 concerns a device for measurement of the electrical impedance of organic and biological materials, such as tissues from vegetable or animal origin. In theory this device might allow the derivation of the susceptance of the measured material, but is not intended for or suited to measuring the moisture of stratum corneum, as it is based on preferably using high frequency and its use moreover involves wetting stratum corneum in order that the contribution therefrom should be the least possible. Primarily, this device is suited with a measurement method for measuring the deep layers of the skin in order to detect skin irritations.

The argument in favour of using high frequencies for measuring skin moisture has been in order to reduce the effect of ionic conductivity in the sweat pores. Consequently the susceptance has been considered to be the electrical parameter which has the most explicit relation to the hydration of the stratum corneum. On a theoretical basis, however, it can be demonstrated that the susceptance should be measured with low frequency methods for an isolated measurement of the stratum corneum.

SUMMARY OF THE INVENTION

The object of the present invention is to eliminate disadvantages involved in the use of the prior art and known instruments for determining the water content of the stratum corneum by means of electrical measurements of the skin. A second object is to perform the measurements at lower frequencies in order to ensure that the measurement results are dominated by the stratum corneum. Yet another object is to be able to differentiate between susceptance and conductance in the measurements, since the conductance is affected by the activity of the sweat glands, the susceptance thus being the most suitable parameter for evaluating skin moisture.

The above-mentioned and other objects are achieved by a method according to the invention which is characterized by measuring the susceptance in the keratinous layer (stratum corneum) under the electrode or electrodes, and with an apparatus for implementing the method according to the invention, characterized in that the M-electrode is connected via an inverting input of a transresistance amplifier to a input of a synchronous rectifier, the synchronous rectifier's reference input being connected to the cosine voltage output of the oscillator, whereby a susceptance signal is obtained on the output of the synchronous rectifier as a measurement signal from the M-electrode.

Advantageous embodiments of the invention are disclosed in the appended dependent claims.

BRIEF DESCRIPTION OF THE DRAWINGS

The invention will now be described in more detail in connection with an embodiment and with reference to the drawing, in which.

DETAILED DESCRIPTION OF THE PREFERRED EMBODIMENTS

Figure 1:
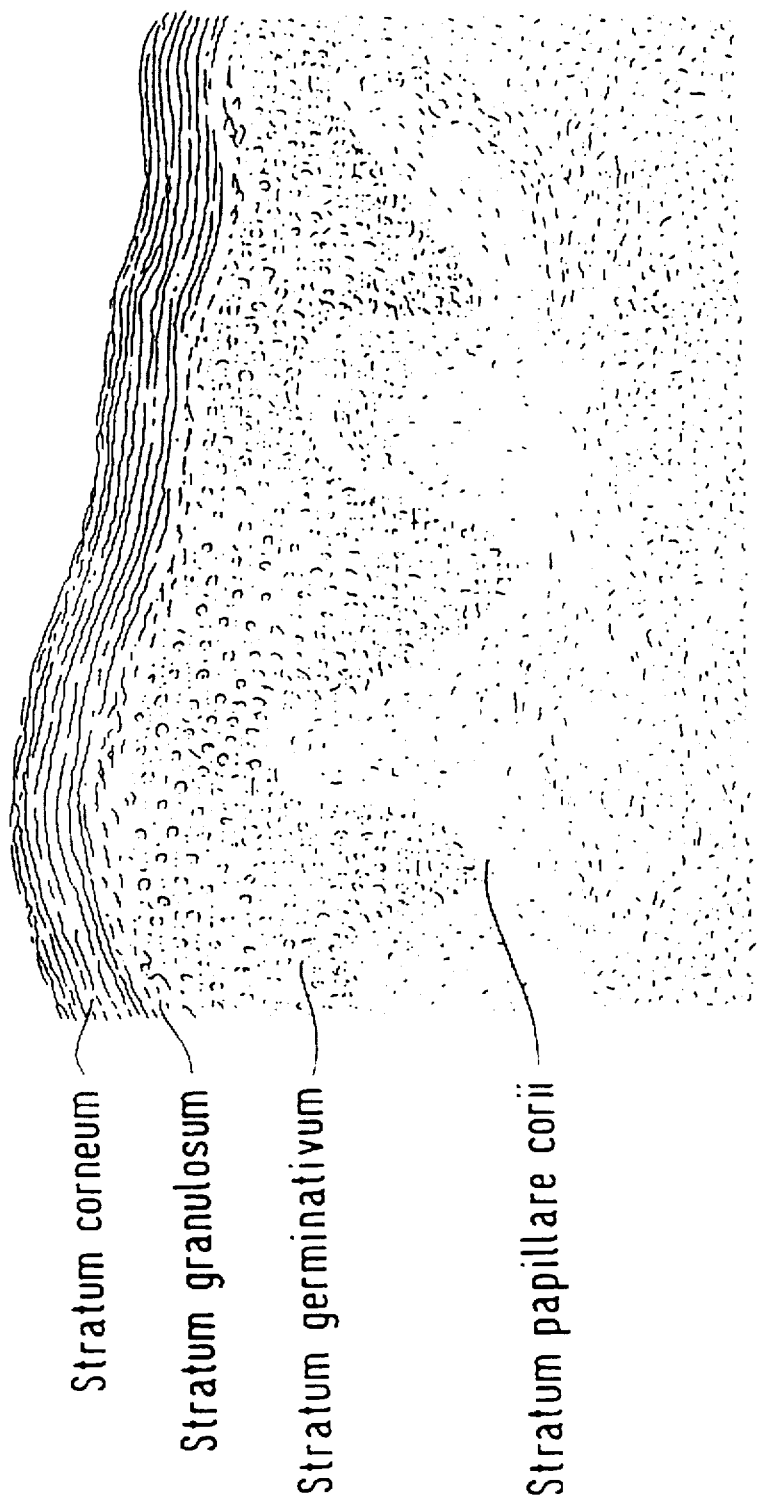
FIG. 1 is a section through the skin of a person, in casu the skin of the shoulder.

FIG. 1 shows a section through the skin of a person, the stratum corneum or keratinous layer being the upper, outer layer of the skin. To be more specific, FIG. 1 represents a section through the skin in the shoulder region of a person. Below the keratinous layer lies the stratum granulosum or granular cell layer and under this the stratum germinativum which is the deepest layer of the epidermis, while the stratum papillare corii forms the transition to the dermis.

Figure 2:
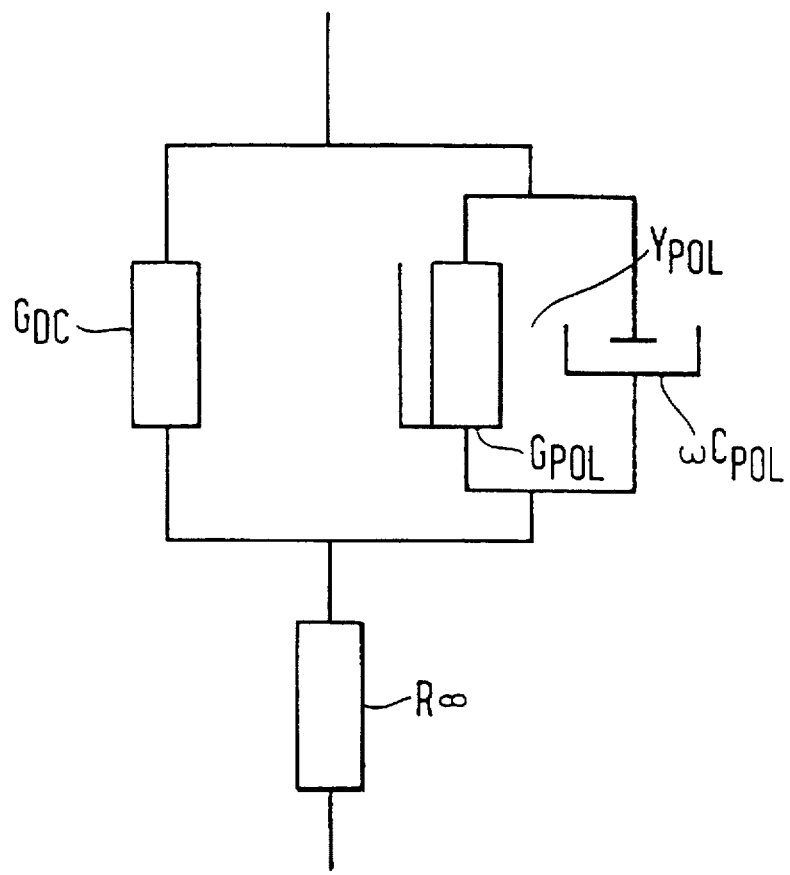
FIG. 2 illustrates a frequently used electrical equivalent circuit for the skin.

FIG. 2 is an electrical equivalent diagram for the skin, where $Y_{POL}$ is the keratinous layer's polarization admittance, consisting of the polarization conductance $G_{POL}$ and the polarization susceptance $\omega C_{POL}$ respectively, and $G_{DC}$ is the keratinous layer's ohmic conductance which is principally attributable to ionic conductance in the keratinous layer's sweat pores. R∞ indicates the resistance in the deeper skin layers.

Figure 3:
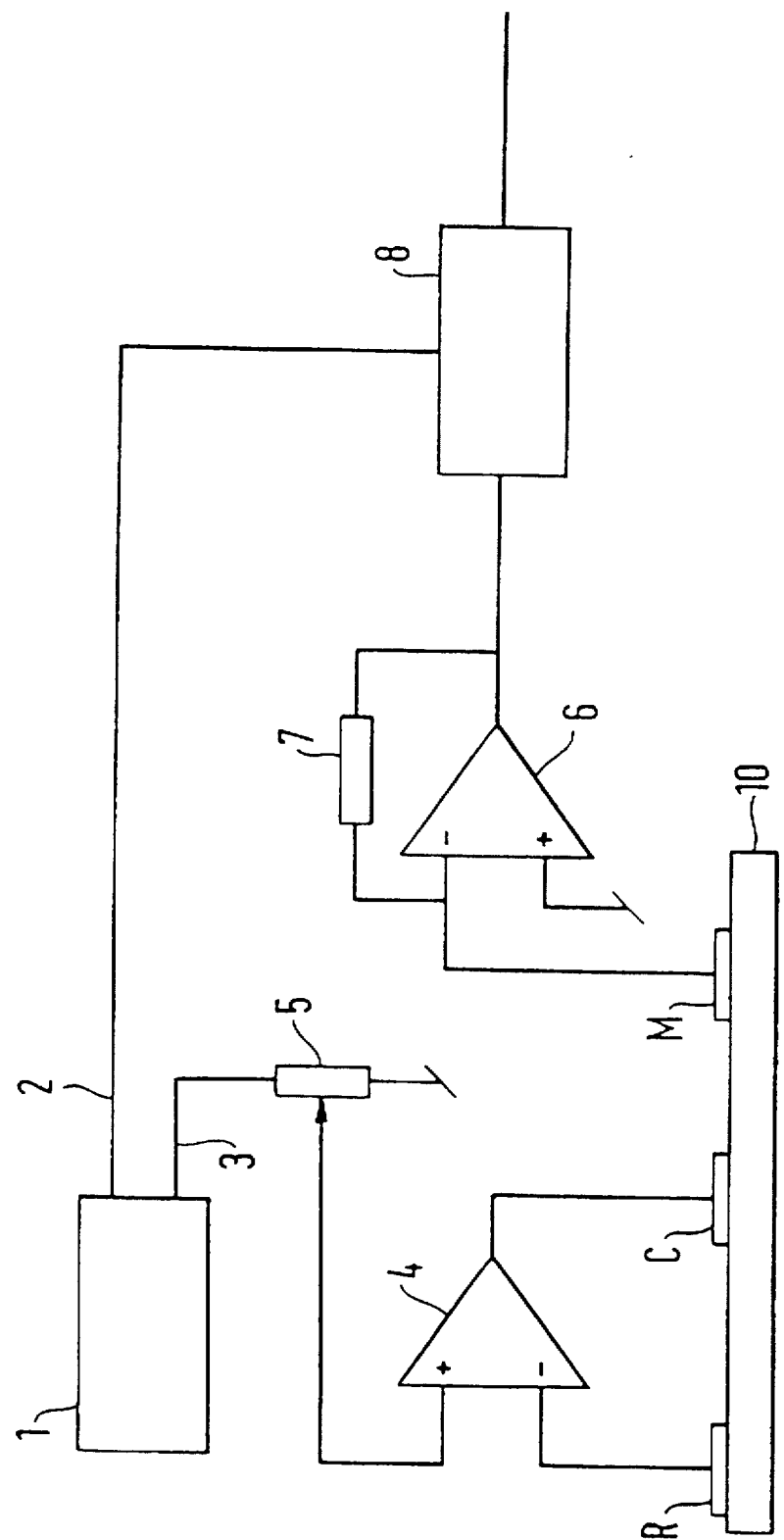
FIG. 3 illustrates an apparatus for implementing the method according to the present invention.

FIG. 3 is a block diagram for the apparatus according to the invention. It comprises a quadrature oscillator 1 whose output voltage frequency is preferably in the range 10–1000 Hz. A sine output 3 of the oscillator 1 is connected to a variable resistor 5, while a cosine output 2 of the oscillator 1 is connected to the reference input of a synchronous rectifier 8. The apparatus comprises three electrodes R, C and M. The principle of such a three-electrode system is described in Grimnes S., "Impedance measurement of individual skin surface electrodes", Med. & Biol. Eng. & Computing, vol. 21, 1983, pp. 750–55 and in Martinsen Ø. G., Grimnes S., and Karlsen J., "An instrument for the evaluation of skin hydration by electrical admittance measurement", Innovation et Technologie en Biologie et Medecine, vol. 14, no. 5, 1993, pp. 588–96.

The R-electrode is connected to an inverting input and the C-electrode to the output of an operational amplifier 4 whose non-inverting input is connected to the variable resistor 5 and thereby the sine voltage output 3 of the oscillator 1. The variable resistor 5 determines the amplitude of the measuring voltage. The R- and C-electrodes may be short-circuited, i.e. connected with each other without affecting the operations of the apparatus. The M-electrode is connected to the inverting input of a transresistance amplifier 6 whose output is connected to the input of the synchronous rectifier 8. A feedback resistor 7 is connected in parallel between the transresistance amplifier's inverting input and its output.

When the apparatus is in use, the oscillator 1 supplies the three-electrode system R, C and M with a sine voltage and the synchronous rectifier 8 with a cosine voltage as a reference signal. The current through the measuring electrode M is converted to a voltage by the transresistance amplifier 6, thus avoiding errors caused by a conventional shunt resistance. The use of a three-electrode system in the apparatus according to the invention also prevents the occurrence of any 50/60 Hz noise, caused by leakage capacitance between the test subject and the network. The apparatus according to the invention measures the electrical susceptance in that part of the stratum corneum which is located beneath the M-electrode. The measurement is not affected by susceptance changes under the two other electrodes R, C and is therefore truly monopolar.

The apparatus according to the invention is preferably designed with a concentric electrode where the inner electrode is used as the M-electrode and the outer as the R-electrode. The concentric electrode is made of metal, preferably an inert metal such as platinum. The C-electrode, for example, can be in the form of an Ag/AgCl solid gel electrode which is attached to another point on the skin. The polarization impedance between a concentric platinum electrode and the skin has previously been found to be negligible, and the use of the preferred concentric electrode with the M- and R-electrodes made of the same type of metal avoids possible errors such as direct current potentials due to different electrode materials and skin potentials when measuring the skin's admittance.

When performing the measurement, a reading is taken of the susceptance value just a few seconds after the electrodes have been applied. An effective measuring voltage of under 500 millivolts RMS was preferably used between the M- and the R-electrodes.

In order to ensure that it really is the susceptance value of the stratum corneum which is being measured, according to the invention a periodic voltage, e.g. a sine voltage is applied between the M-electrode and the C-electrode with a frequency of under 50 kHz and preferably under 1 kHz. However, there is no reason why the frequency of the periodic voltage cannot be considerably lower. At the same time an effective measuring voltage of under 500 millivolts RMS is applied between the M- and the R-electrodes. In order to differentiate between susceptance and conductance, as already mentioned a synchronous rectifier 8 is used connected to the M-electrode and the oscillator 1 respectively, the synchronous rectifier 8 as reference being supplied with a cosine voltage from the oscillator 1.

In an experimental test of the method and the apparatus according to the present invention the effect of two different liposome formulations with 15 mg/ml and 150 mg/ml liposome was measured over a period of 3 hours. A comparison was performed of the measurements implemented according to the present invention with measurements performed with the "Corneometer CM 820", a well-known commercial instrument which measures the skin's capacitive character and shows it in arbitrary units. In the tests the liposomes were manufactured by means of phosphoric lipids supplied by the company Sigma Chemical Co., a film method being used for the manufacture which gave an average diameter of 85 nm for the liposomes. In the measurement tests the apparatus and the method according to the present invention showed a significant increase in the measured susceptance values for skin areas treated with both liposome formulations, while the "Corneometer" only showed a statistically significant difference for the formulation of 150 mg/ml.

Consequently the method and the apparatus according to the present invention are well suited to the detection of small alterations in the hydration of the stratum corneum, since they react to even small changes in the moisture level.

We claim:

1. A method for measuring the moisture content in skin, comprising:

contacting the skin with three electrodes, wherein at least one measuring electrode is placed on the skin where the moisture has to be measured and the remaining two electrodes on the skin adjacent thereto;

applying a periodic voltage with a frequency of less than 50 kHz to the electrodes; and measuring the susceptance in the skin under at least one electrode.

2. The method according to claim 1, wherein said applying step comprises applying a periodic voltage between the measuring electrode and a first remaining electrode, and said measuring step comprises measuring the susceptance beneath the measuring electrode.

3. The method according to claim 2, wherein said measurement is monopolar.

4. The method according to claim 1 or 2, wherein said moisture content is measured in the keratinous layer.

5. The method according to claim 1 or 2, wherein said applying step comprises applying a sine voltage with a frequency of less than 1000 Hz.

6. The method according to claim 2, wherein said measuring step further comprises measuring said susceptance with an effective measuring voltage between the measuring electrode and the second remaining electrode of less than 500 mV RMS.

7. The method according to claim 2, wherein said measuring step further comprises differentiating between susceptance and conductance by using a synchronous rectifier connected to the measuring electrode and an oscillator respectively, and applying a reference cosine voltage to the synchronous rectifier from the oscillator.

8. The method according to claim 2, further comprising short-circuiting the first and second remaining electrodes.

9. An apparatus for performing a method for measuring the moisture content in skin, especially in the keratinous layer (stratus corneum), wherein three electrodes are used, wherein at least one electrode is the measurement electrode and is adapted to be placed on the skin where the moisture has to be measured, and wherein a periodic voltage with a frequency of less than 50 kHz is applied to the electrodes, wherein the apparatus comprises:

a measuring electrode and first and second remaining electrodes, wherein the second remaining electrode is connected to an inverting input and the first remaining electrode to the output of an operational amplifier, the operational amplifier's non-inverting input being connected to a sine voltage output of an oscillator; and wherein the measuring electrode is connected via an inverting input of a transresistance amplifier to an input of a synchronous rectifier, the synchronous rectifier's reference input being connected to a cosine voltage output of the oscillator, whereby a susceptance signal is obtained on the output of the synchronous rectifier as a measurement signal from the measuring electrode.

10. The apparatus according to claim 9, wherein the oscillator is a quadrature oscillator, the oscillator's output voltages having a frequency in the range 10–1000 Hz.

11. The apparatus according to claim 9, wherein the measuring electrode and the second remaining electrode are the inner electrode and the outer electrode respectively in a concentric ring electrode made of metal.

12. The apparatus according to claim 11, wherein the measuring electrode and the second remaining electrode are made of the same metal.

13. The apparatus according to claim 12, wherein said metal is an inert metal.

14. The apparatus according to claim 9, wherein the first and second remaining electrodes are short-circuited.

\* \* \* \* \*